US008851741B2

(12) United States Patent
Ganmor et al.

(10) Patent No.: US 8,851,741 B2
(45) Date of Patent: Oct. 7, 2014

(54) EMULSIFIER WITH TWO SHEAR STAGES

(76) Inventors: Shmuel Ganmor, Gedera (IL); Beni Ronen, Ra'anana (IL)

(*) Notice: Subject to any disclaimer, the term of this patent is extended or adjusted under 35 U.S.C. 154(b) by 0 days.

(21) Appl. No.: 13/266,542

(22) PCT Filed: Apr. 18, 2010

(86) PCT No.: PCT/IL2010/000305
§ 371 (c)(1),
(2), (4) Date: Nov. 30, 2011

(87) PCT Pub. No.: WO2010/125558
PCT Pub. Date: Nov. 4, 2010

(65) Prior Publication Data
US 2012/0093906 A1    Apr. 19, 2012

Related U.S. Application Data

(60) Provisional application No. 61/173,227, filed on Apr. 28, 2009.

(51) Int. Cl.
*B01F 7/10*    (2006.01)
(52) U.S. Cl.
USPC ................ 366/171.1; 366/172.1; 366/304
(58) Field of Classification Search
USPC ............... 366/64, 96–99, 303, 304, 315–317,
366/168.1, 171.1, 172.1, 172.2, 181.7,
366/176.1–176.2; 241/261, 261.2, 188.2
See application file for complete search history.

(56) References Cited

U.S. PATENT DOCUMENTS

| 2,882,149 | A | * | 4/1959 | Willems ........................ 241/80 |
| 3,081,069 | A | * | 3/1963 | Oakes .......................... 366/304 |
| 3,190,567 | A | * | 6/1965 | Willems ....................... 241/162 |
| 3,940,115 | A | * | 2/1976 | Zipperer ....................... 366/303 |
| 3,976,087 | A | * | 8/1976 | Bolton et al. .............. 137/15.01 |
| 4,231,666 | A | * | 11/1980 | Baron ........................... 366/304 |
| 4,281,937 | A | * | 8/1981 | Ferri et al. .................... 366/303 |
| 4,533,254 | A | * | 8/1985 | Cook et al. ................. 366/176.1 |
| 4,785,013 | A |  | 11/1988 | Margossian |
| 4,915,509 | A | * | 4/1990 | Sauer et al. ................. 366/171.1 |
| 5,632,596 | A |  | 5/1997 | Ross |
| 5,931,579 | A | * | 8/1999 | Gallus et al. ............... 366/163.2 |
| 7,022,651 | B1 |  | 4/2006 | Lightcap et al. |

(Continued)

FOREIGN PATENT DOCUMENTS

| JP | 57021924 | 2/1982 |
| JP | 58216726 | 12/1983 |
| WO | WO 8001469 A1 * | 7/1980 ................ B01F 3/12 |

OTHER PUBLICATIONS

International Search Report of Application No. PCT/IL2010/000305 mailed on Aug. 30, 2010.

*Primary Examiner* — Charles Cooley
(74) *Attorney, Agent, or Firm* — Pearl Cohen Zedek Latzer Baratz LLP

(57) ABSTRACT

An agricultural system including an emulsifier, an oils and additives tank, an oils and additives feed pump, a water tank, a water feed pump, a spray pump, and at least one spay nozzle, wherein the agricultural system is configured for shearing oil drops into oil droplets at a first mechanical shear stage of the emulsifier and forcing the oil, the additive, and the water by centrifugal force for shearing the oil droplets at a second mechanical shear stage of the emulsifier into oil emulsion droplets against a centrifugal force.

6 Claims, 9 Drawing Sheets

(56) References Cited

U.S. PATENT DOCUMENTS

| | | | |
|---|---|---|---|
| 8,079,752 B2 * | 12/2011 | Rausch et al. | 366/178.2 |
| 8,491,848 B2 * | 7/2013 | Gandhi et al. | 366/304 |
| 8,702,298 B2 * | 4/2014 | Sei | 366/136 |
| 2004/0161400 A1 | 8/2004 | Hiromoto | |
| 2004/0170084 A1 * | 9/2004 | Choi et al. | 366/304 |
| 2006/0008495 A1 | 1/2006 | Newman | |
| 2011/0250635 A1 * | 10/2011 | Paz Briz et al. | 435/41 |
| 2012/0093906 A1 * | 4/2012 | Ganmor et al. | 424/405 |

* cited by examiner

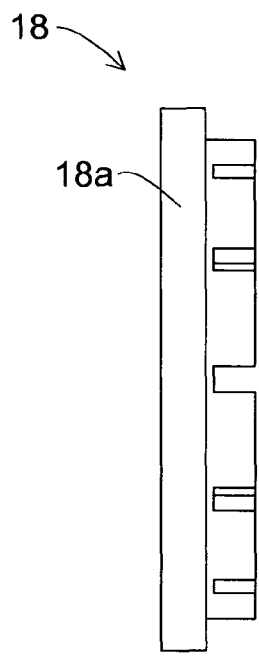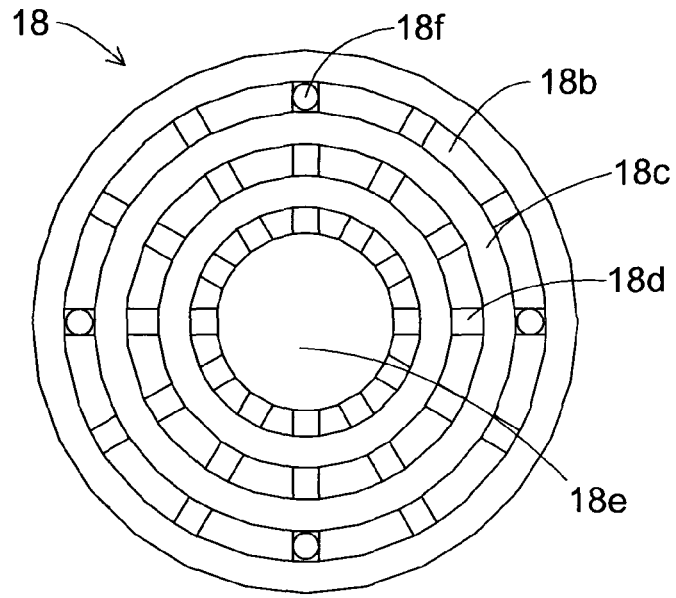
Fig. 7    Fig. 8
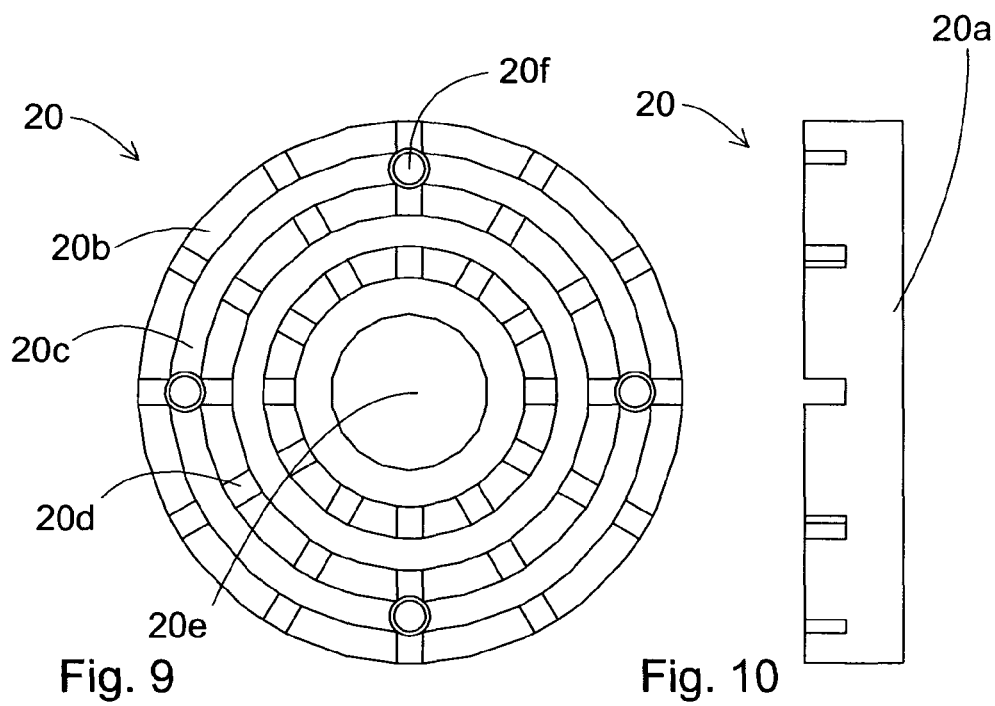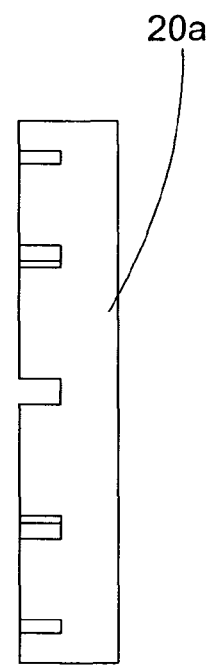
Fig. 9    Fig. 10

EMULSIFIER WITH TWO SHEAR STAGES

CROSS-REFERENCE TO RELATED APPLICATIONS

This application is a National Phase Application of PCT International Application No. PCT/IL2010/000305, International Filing Date Apr. 18, 2010, entitled "Emulsions, Emulsifier, Method of Use and Production Process", published on Nov. 4, 2010 as International Publication Number WO 2010/125558, claiming priority of U.S. Patent Application No. 61/173,227, filed Apr. 28, 2009, both of which are incorporated herein by reference in their entirety.

FIELD OF THE INVENTION

The present invention relates to emulsion preparation.

BACKGROUND OF THE INVENTION

Farmers and growers all over the world are faced with pests, insects and diseases that may harm the plants, their leaves and their fruits. In order to combat these threats farmers can use pesticides and insecticides by applying them onto the foliage.

"Organic" growers are usually reluctant to use pesticides and insecticides, as they are considered to be harmful to humans and animals. The "organic" growers would usually prefer to use non-toxic pesticides and insecticides whenever possible.

It is well known, and has been in practice for many years now, that botanical oils such as almond oil, soy bean oil, cotton seed oil, castor oil and canola oil, for example, can be used as pesticides and insecticides and to control certain diseases common in agriculture. Many botanical seeds and beans contain minute amounts of highly toxic agents. For example, the almond seeds contain cyanide and the castor seeds contain ricin both of which are highly toxic in large quantities, yet are not harmful to humans in small doses and are used as a natural defense mechanism by the plants against pests and insects.

In order to effectively deliver the botanical oils to the plants as pesticides and insecticides, they must be emulsified with water. This emulsification creates tiny droplets of oil in the water allowing the farmers to spray the emulsion onto the plants using standard spraying mechanisms.

Several methods of producing such emulsions are known and used in agriculture these days:

High pressure emulsifiers operate with high pressure oil injected into water stream through a porous filter in order to shear the oil into small droplets. The oil pressure in these systems may go up to 2000 BAR (over 29000 PSI) or even beyond that. Droplet size coming out of such emulsifiers is typically about 1 micron average diameter. An example for such a high pressure emulsifier is the EmulsiFlex-055, made by Avestin Inc.

A second technique involves high shear emulsifiers which use a two part mechanism—a stator and rotor where the rotor rotates within the stator. The stator and rotor are placed in a heated container containing a mixture of water and oil. When the rotor rotates within the stator while in the container, the oil is thrown from the inner part of the rotor to its outer side through the rotor by centrifugal forces and due to the shape of the rotor and stator; the oil is sheared into small drops. As the process continues on, the oil drops are sheared repeatedly, creating smaller and smaller droplets. The main disadvantage of the high shear emulsifiers is that there is very little consistency in the size of the oil droplets within the emulsion unless the process is continued for a very long time. An example of high shear emulsifier is the ZGF210 made by Shanghai Chengxing M&E Co., Ltd.

SUMMARY

It would be advantageous to have a technique that produce an emulsion with a high degree of consistency in the droplet size that can be achieved with a low pressure oil intake and short production duration. None of the prior art devices comprises all of the above characteristics and functions.

There is therefore a need for an emulsifier and emulsion, which comprise a combination of all of the above characteristics and functions.

The present invention relates to emulsion preparation, in a manner that also grants important benefits to agricultural application, however is not in any way limited to only agricultural application.

The background art does not teach or suggest an emulsion with a high degree of consistency in the droplet size that can be achieved with a low pressure oil intake and short production duration nor does it teach or suggest an emulsifier to produce such emulsion.

The present invention overcomes these deficiencies of the background art by providing an emulsifier that uses three main stages in the preparation of the above mentioned emulsion.

An embodiment of the present invention is described herein below in which there are two tanks feeding the emulsifier. The first tank is used to hold a mixture of oil, oil and surfactants, or oils and additives or additives and the second tank holds water that can be heated within the tank by means of a water heater. The efficiency of the emulsifier can be increased by using hot water.

The oils and additives are injected into the oil and additives intake and are compressed into a porous filter. The water is injected into the water intake. As the oils and additives exit the porous filter, the water flow detaches the oils and additives from the filter surface creating drops of oils and additives in the water.

The mixture of water and oils and additives drops is then compressed through a narrow channel and into the center of the first rotor and first stator assembly. As the first rotor rotates within the first stator, the water, oils, and additives mixture is forced outwards by the centrifugal force, causing some of the liquid to pass in a relatively short time. As the mixture moves outwards, the first rotor and first stator shear the oils and additives' drops into smaller droplets.

Once the mixture reaches the outer rim of the first rotor and first stator assembly it is compressed through the intermediate channel into the outer rim of the second rotor and second stator assembly. Here, the mixture is compressed into the second rotor and second stator assembly in an opposite direction to the centrifugal force. Compressing the mixture opposing the centrifugal force takes the same time duration for all the liquid, causing the mixture to spend relatively long time within the second rotor and second stator assembly causing it to shear more times and more evenly, thus, eventually create droplets, which are very small and consistent in size.

Once the mixture reaches the center of the second rotor and second stator assembly, it is already an emulsion ready for use. It is compressed out of the emulsifier through the discharge channel and emulsion discharge pipe.

The emulsion can then be put into a transportation tank to be delivered to the end consumer for use, or if installed onto an agricultural machine such as a sprayer, it may be pumped out by a spray pump into spray nozzles and onto the foliage to be treated.

One of the most important properties of the method of use of the emulsions according to the present invention is the very short time typically used between the production and the application in the field. This in turn minimizes time related deterioration of the emulsion such as oxidation and increase of acidic materials within the emulsion. Acidic materials within the emulsion and oxidation may cause burns on foliage and on vegetables and fruits.

By using the emulsions within a short time from the time of production (up to 24 hours from production without refrigeration or up to a week with refrigeration at five degrees Celsius) the concentration of acidic materials can be limited to less than one percent, less than eight tenths of a percent, less than six tenths of a percent, less than four tenths of a percent, less than two tenths of a percent or practically no acidic materials within the emulsion. The percentage mentioned above is of the total weight of the emulsion.

According to the present invention a method for preparation and use of emulsions is provided. The method including the stages of (a) injecting water, oil and additive into an emulsifier; (b) shearing the oil into oil emulsion droplets; and (c) discharging final emulsion product outside of the emulsifier, wherein the oil is a botanical oil, wherein the oil emulsion droplets have a volume medium diameter, and wherein said volume medium diameter is typically more than one micron and less than fifteen microns.

According to another feature of the present invention the method further comprising the stage of: (d) spraying the emulsions on vegetation, wherein the volume medium diameter is at least one micron and at most fifteen microns.

According to another feature of the present invention of the method for preparation and use of emulsions, the spraying is done at most twenty-four hours after the discharging.

According to another feature of the method for preparation of emulsions of the present invention, the emulsion contains at most two-tenths percent of acidic material, for the emulsion weight.

According to another feature of the method for preparation of emulsions, of the present invention, the emulsion is substantially free of acidic materials.

According to another feature of the present invention, the emulsion is used for protection of crops against pests including insects, diseases, fungi and viruses.

According to another feature of the present invention, the emulsions are kept in cool conditions, and wherein the spraying is done within at most one week.

According to the present invention there is provided a process for producing emulsion including the stages of: (a) injecting oil and additive into the oil intake of an emulsifier; (b) compressing the oil and the additive into a porous filter of the emulsifier; (c) injecting heated water into a water intake of the emulsifier; (d) shearing the oil into oil drops by the water and mixing the oil, the additive and the water; (e) shearing the oil drops into oil droplets at a first mechanical shear stage of the emulsifier and forcing the oil, the additive and the water by a centrifugal force; (f) compressing the oil, the additive and the water into a second mechanical shear stage of the emulsifier; (g) shearing the oil droplets at the second mechanical shear stage of the emulsifier into oil emulsion droplets against a centrifugal force; and (h) discharging a final emulsion product outside of the emulsifier.

According to another feature of the present invention the process for producing emulsion of the present invention the oil is botanical oil, wherein the oil emulsion droplets have a volume medium diameter, and wherein the volume medium diameter is at least one micron and at most fifteen microns.

According to another feature of the process for producing emulsion for agricultural use, of the present invention, the emulsion contains at most two-tenths of percent of acidic material, for the emulsion weight.

According to another feature of the process for producing emulsion, of the present invention, the emulsion is substantially free of acidic materials.

According to another feature of the process for producing emulsion of the present invention, the emulsion has liquid fractions and wherein the emulsion flows inside the second mechanical shear stage against centrifugal forces, resulting in even passage time for the liquid fractions.

According to the present invention there is provided an emulsion for agricultural use including: (a) at least one oil; and (b) water, wherein the oil is in droplets phase, wherein the oil droplets have a volume medium diameter, wherein the volume medium diameter is at least one micron and at most fifteen microns.

According to another feature of the emulsion according to the present invention, the at least one oil is a botanical oil.

According to another feature of the emulsion according to the present invention, the at least one oil is an edible botanical oil.

According to still another feature of the emulsion according to the present invention, the at least one oil is selected from a group consisting of peanut oil, cottonseed oil, neem oil, soybean oil, canola (rapeseed) oil, sunflower oil, olive oil, sesame oil, corn oil, linseed oil, palm kernel oil, rice bran oil, grape seed oil, tea tree oil, pumpkin seed oil, argan oil, limeseed oil, nut oils, eucalyptus oil, citronella oil, and citrus oil.

According to still another feature of the emulsion according to the present invention, the percentage of the at least one oil is at most ten percent of the emulsion.

According to still another feature of the emulsion according to the present invention, the emulsion of claim further includes: (c) at least one additive, wherein the percentage of the at least one additive is at most six-tenths of percent for the emulsion weight.

According to still another feature of the emulsion according to the present invention, the emulsion contains at most two-tenths percent of acidic material, for the emulsion weight.

According to still another feature of the emulsion according to the present invention, the emulsion is substantially free of acidic materials.

According to still another feature of the emulsion according to the present invention the at least one oil is a fish oil.

According to the present invention there is provided an agricultural system comprising: (a) an emulsifier, wherein the emulsifier includes: (i) a casing, having water intake, oil intake, and discharge channel; (ii) a pivot axis for transferring rotational motion from an engine to at least one rotational element of the emulsifier, mounted at least partially within the emulsifier; (iii) a porous filter mounted within the emulsifier so that when oil is injected and forced to flow through the oil intake, the oil flows through the porous filter into a tight fit space between said pivot axis and said porous filter; and (iv) a first mechanical shear stage mounted inside the emulsifier.

According to another feature of the present invention the first mechanical shear stage includes: a first stator having a first stator base and at least two first stator annular rings attached to the first stator base, wherein between every two adjacent of the first stator annular rings there is a first stator annular channel, and wherein the first stator has at least one first flow channel, crossing the first stator annular rings; and a first rotor having a first rotator rotor base and at least two first rotator annular rings attached to the first rotor base, wherein between every two adjacent first rotator annular rings there is a first rotor annular channel, and wherein the first rotor has at least one first rotator flow channel, crossing the first rotor annular rings, wherein the first mechanical shear stage is so arranged that a first rotor annular ring can rotate inside a first rotor annular channel.

According to still another feature of the present invention the emulsifier further includes: (v) a second mechanical shear stage mounted within the emulsifier.

According to still another feature of the present invention the second mechanical shear stage includes: a second stator having a second stator base and at least two second stator annular rings attached to the second stator base, wherein between every two adjacent second stator annular rings there is a second stator annular channel, and wherein the second stator has at least one second flow channel, crossing the second stator annular rings; and a second rotor having a second rotator rotor base and at least two second rotor annular rings attached to the second rotor base, wherein between every two adjacent second rotor annular rings there is a second rotor annular channel, and wherein the second rotor has at least one second rotor flow channel, crossing the second rotor annular rings, wherein the second mechanical shear stage is so arranged that a second rotor annular ring can rotate inside a second rotor annular channel.

According to still another feature of the present invention the first stator is attached to the casing, and wherein the second stator is attached to the casing.

According to still another feature of the present invention the emulsifier further includes: (vi) a rotor disk attached to the pivot axis, wherein the first rotor is attached to the rotor disk and wherein the second rotor is attached to the rotor disk. According to still another feature of the present invention the emulsifier has an intermediate channel between the casing and the first mechanical shear stage, the rotor disk, and the second mechanical shear stage.

According to still another feature of the present invention there is a gap between the first stator annular ring and the first rotor annular ring, wherein the gap is at most one tenth of a millimeter.

According to still another feature of the present invention the casing includes: a main body; a front cover, attached to the main body; and a back cover attached to the main body.

According to still another feature of the present invention the agricultural system further includes: (b) an oils and additives tank; (c) an oils and additives feed pump, wherein the oils and additives tank is operatively connected to the oils and additives feed pump and wherein the oils and additives feed pump is operatively connected to the emulsifier; (d) a water tank; (e) a water feed pump, wherein the water tank is operatively connected to the water feed pump and wherein the water feed pump is operatively connected to the emulsifier; and (f) a spray pump, wherein the emulsifier is operatively connected to the spray pump; and (g) at least one spray nozzle, wherein the spray pump is operatively connected to the at least one spray nozzle.

According to still another feature of the present invention the agricultural system further includes: (b) an oils and additives tank; (c) an oils and additives feed pump, wherein the oils and additives tank is operatively connected to the oils and additives feed pump and wherein the oils and additives feed pump is operatively connected to the emulsifier; (d) a water tank; (e) a water feed pump, wherein the water tank is operatively connected to the water feed pump and wherein the water feed pump is operatively connected to the emulsifier; and (f) a transporting tank, wherein the emulsifier is operatively connected to the transporting tank.

Additional objects and advantages of the invention will be set forth in part in the description which follows and, in part, will be obvious from the description, or may be learned by practice of the invention.

BRIEF DESCRIPTION OF THE DRAWINGS

The invention is herein described, by way of example only, with reference to the accompanying drawings, wherein:

FIG. 7 is a schematic side view of the first stator, according to the present invention.

FIG. 8 is a schematic front view of the first stator, according to the present invention.

FIG. 9 is a schematic front view of the first rotator rotor, according to the present invention.

FIG. 10 is a schematic side view of the first rotor, according to the present invention.

DETAILED DESCRIPTION OF EMBODIMENTS

Figure 1:
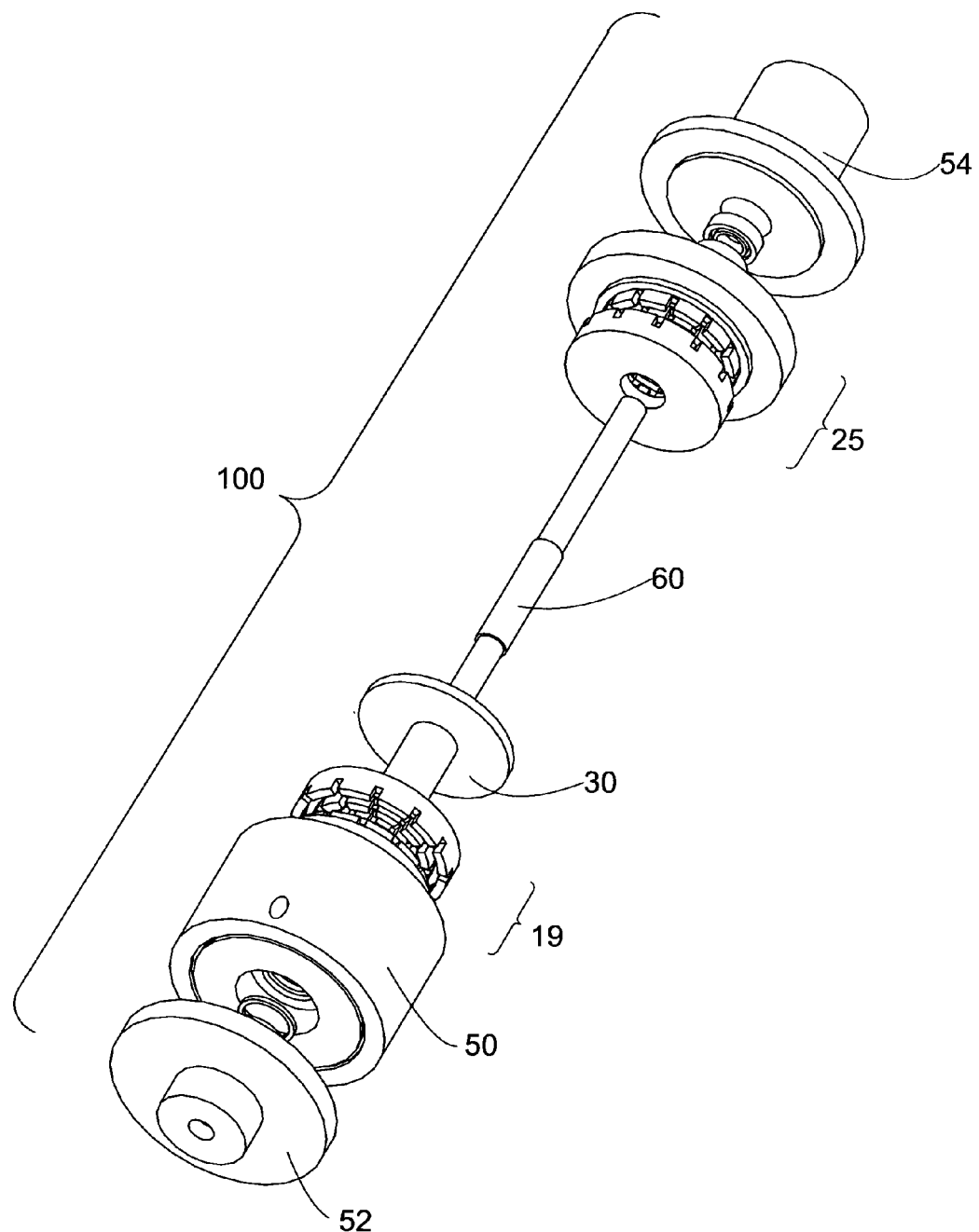
FIG. 1 is an isometric exploded schematic illustration of an exemplary, illustrative embodiment of an emulsifier, according to the present invention.

The present invention is of emulsions, an emulsifier for preparation of the emulsions, a method of use and a production process of the emulsions.

The principles and operation of the emulsifier the production process of the emulsions and the method of use according to the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawings.

Unless otherwise defined, all technical and scientific terms used herein have the same meaning as commonly understood by one of ordinary skill in the art to which this invention belongs. The materials, dimensions, methods, and examples provided herein are illustrative only and are not intended to be limiting.

The following list is a legend of the numbering of the application illustrations:

10 water intake
11 water flow path
12 oil intake
13 oil and additives flow path
14 porous filter
15 mixture flow path
16 tight fit space
18 first stator
18a first stator base
18b first stator annular ring
18c first stator annular channel
18d first stator flow channel
18e first stator pivot axis opening
18f first stator fastening screw hole
19 first mechanical shear stage
20 first rotor
20a first rotor base
20b first rotor annular ring
20c first rotor annular channel
20d first rotor flow channel
20e first rotor pivot axis opening
20f first rotor fastening screw hole
22 intermediate channel
24 second rotor
24a second rotor base
24b second rotor annular ring
24c second rotor annular channel
24d second rotor flow channel
24e second rotor pivot axis opening
24f second rotor fastening screw hole
25 second mechanical shear stage
26 second stator
26a second stator base
26b second stator annular ring
26c second stator annular channel
26d second stator flow channel
26e second stator pivot axis opening
26f second stator fastening screw hole
27 discharge channel
28 emulsion discharge pipe
30 rotor disk
50 main body
52 front cover
54 back cover
56 casing
60 pivot axis
100 emulsifier
102 oils and additives feed pump
104 oils and additives tank
106 water tank
108 heating element
110 water feed pump
112 transporting tank
114 spray nozzle
116 spray pump
1000 agricultural system Referring now to the drawings, FIG. 1 is an isometric exploded schematic illustration of an exemplary, illustrative embodiment of an emulsifier 100, according to the present invention.

FIG. 1 depicts the main components of the emulsifier 100 such as the front cover 52, the main body 50, the first mechanical shear stage 19, and the rotor disk 30, the pivot axis 60, the second mechanical shear stage 25 and the back cover 54. During assembly, the first rotor 20 and second rotor 24 are attached to the rotor disk 30 using several rotor attachment screws (not shown in this figure) so that when the pivot axis 60 rotates, it rotates the rotor disk 30 and with it, the rotors rotate together as well.

The main body 50, the front cover 52 and the back cover 54 comprise the casing 56 of the emulsifier 100, however, this is should not limit the present invention to this specific structure and it is possible to have a casing 56 composed of different elements.

Similarly, the rotational movement is transferred from the pivot axis 60 to rotor disk 30 (for example by means of a tenon and mortise) and to the first rotor 20 and second rotor 24. This description does not limit the present invention to this specific structure and other configurations may be applied to transfer the rotational movement from the pivot axis 60 to the first rotor 20 and second rotor 24, for example, by directly transferring the movement from the pivot axis 60 to the first rotor 20 and second rotor 24, without the use of the rotor disk 30. In this case, the first rotor 20 and second rotor 24 may be connected to each other and possible even manufactured as a single element together with the pivot axis 60.

Similarly, the present invention is not limited to the structure of the different components of the emulsifier 100 as they appear in the present figure and especially, it does not limit the manufacture and use of several components shown in the present figure as discrete components, but may be in a single element comprising the different functions of the discrete components.

Figure 2:
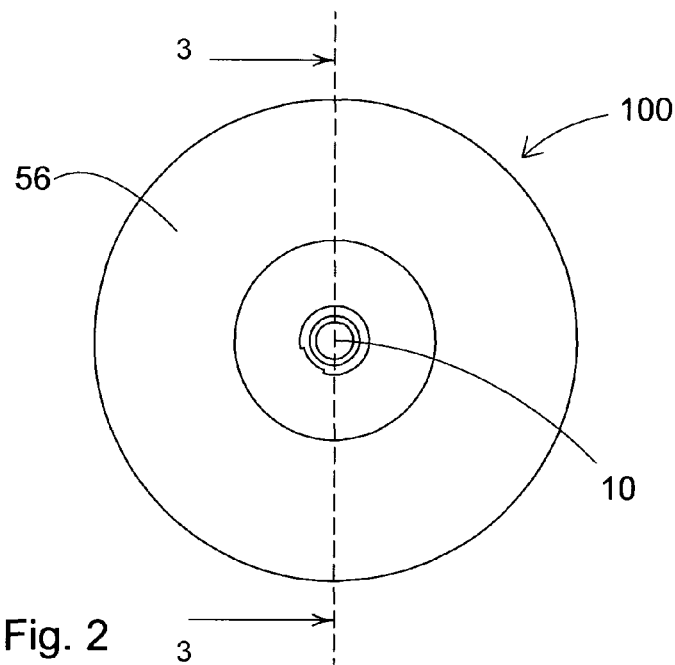
FIG. 2 is a front view schematic illustration of an exemplary, illustrative embodiment of an emulsifier, according to the present invention, upon which the section plane 3-3 is marked.

FIG. 2 is a front view schematic illustration of an exemplary, illustrative embodiment of an emulsifier 100, according to the present invention, upon which the section plane 3-3 is marked. From the front view, it's possible to see the casing 56 and the water intake 10 opening.

Figure 3:
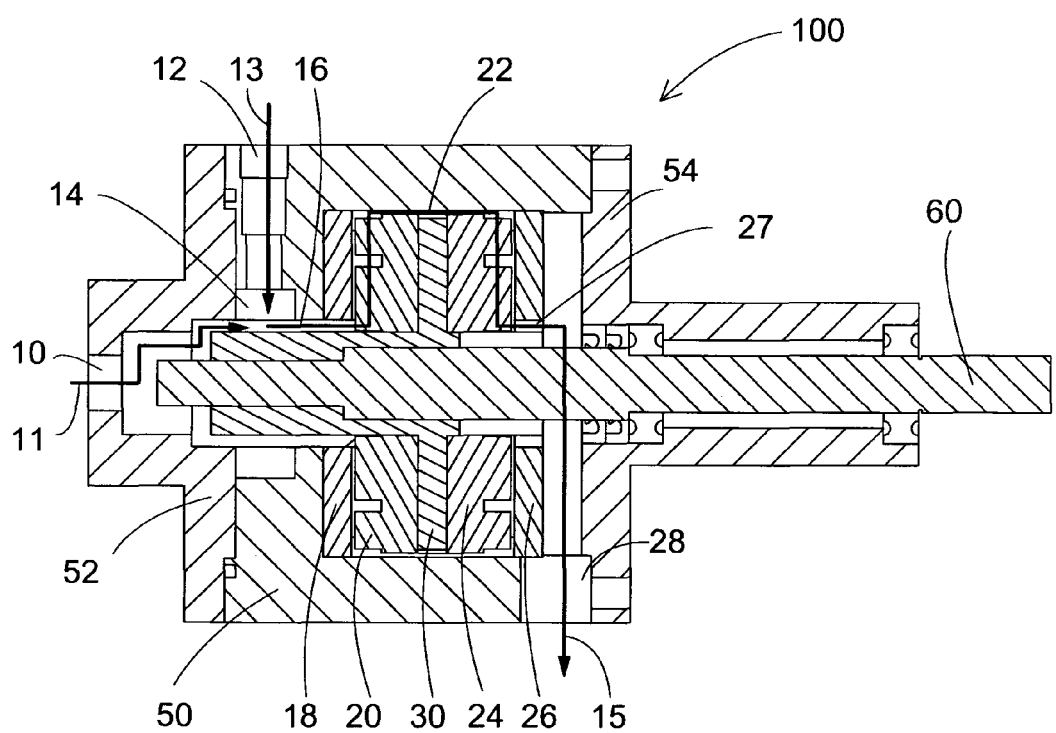
FIG. 3 is a cross sectional view 3-3 through the emulsifier of FIG. 2, according to the present invention.

FIG. 3 is a cross sectional view 3-3 through the emulsifier 100 of FIG. 2, according to the present invention.

This figure depicts the emulsifier 100 in its assembled state as well as the water flow path 11, the oil and additives flow path 13 and the mixture flow path 15 through the various sections of the emulsifier.

First the oils and additives are injected into the oil intake 12 and compressed into the porous filter 14. At the same time, heated water is injected into the water intake 10. Next, the water shears the oils and additives into drops as they exit the porous filter 14 and is mixed in the tight fit space 16 (between the pivot axis 60 and the porous filter 14). The mixture is compressed into the first mechanical shear stage 19 where the rotational movement of the first rotor 20 within the first stator 18 causes the mixture to be sheared into droplets and is forced outwards by the centrifugal force in a relatively short time and is then compressed into the intermediate channel 22. From there, the mixture is compressed into the second mechanical shear stage 25 in an opposite direction to the centrifugal force. Compressing the mixture opposing the centrifugal force takes a relatively long time causing the mixture to spend more time within the second mechanical shear stage 25 causing it to shear more times and eventually create droplets which are very consistent in size. The final emulsion product is discharged through the discharge channel 27 and emulsion discharge pipe 28 outside of the emulsifier 100.

The distance between the rotor and stator d1 (shown in FIG. 12) ensures that shearing will occur and create the desired droplet size. In addition, the rotational speed of the first rotor 20 and second rotor 24, together with the initial temperature of the injected water has an effect on the droplet size and consistency.

Achieving the desired droplet size and consistency may require some trial and error experiments, however laboratory tests showed that rotating the pivot axis 60 (and with it the first rotor 20 and second rotor 24) at 6000 rpm together with water temperature of approximately 25 degrees Celsius generates an adequate droplet size.

Additionally, laboratory tests showed that increasing the rotational speed of the pivot axis 60 or decreasing the margin between the stators and rotors d1 decreases the droplet size.

Figure 4:
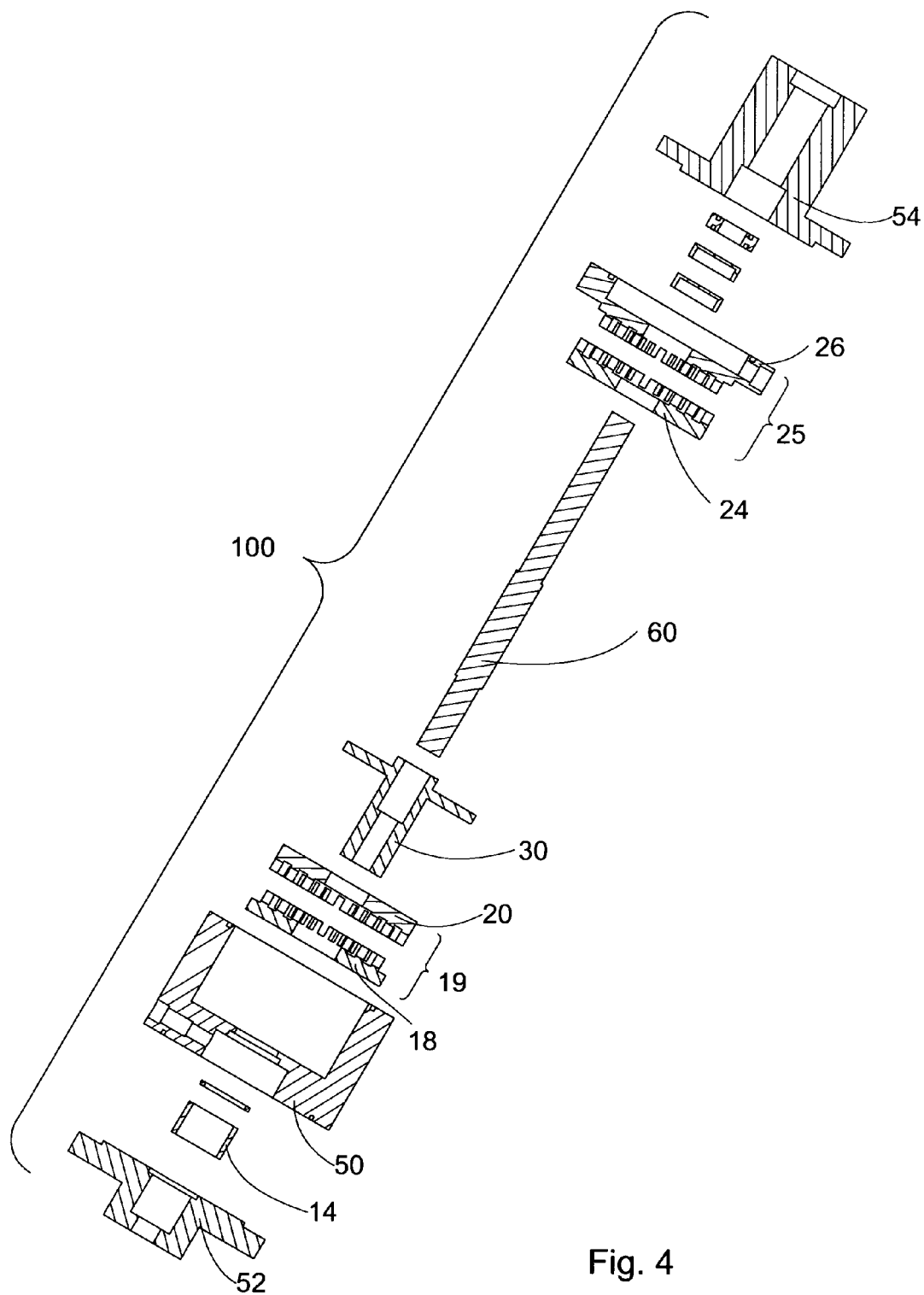
FIG. 4 is an exploded cross sectional view 3-3 through the emulsifier of FIG. 2, according to the present invention.

FIG. 4 is an exploded cross sectional view 3-3 through the emulsifier 100 of FIG. 2, according to the present invention.

This figure depicts how the different components of the emulsifier are located with respect to one another.

Figure 5:
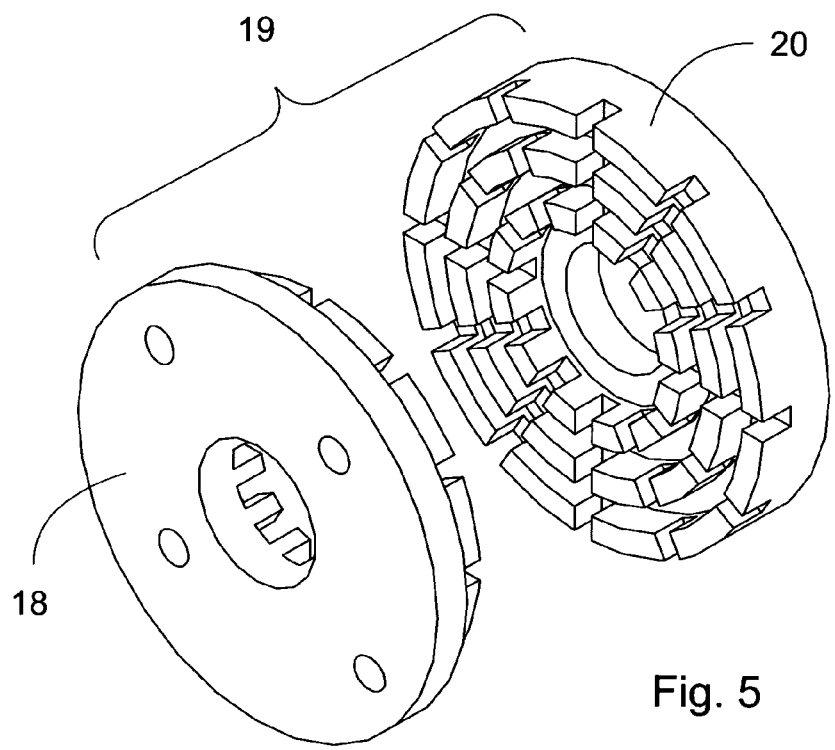
FIG. 5 is an isometric exploded front view of the first mechanical shear stage, according to the present invention.
Figure 6:
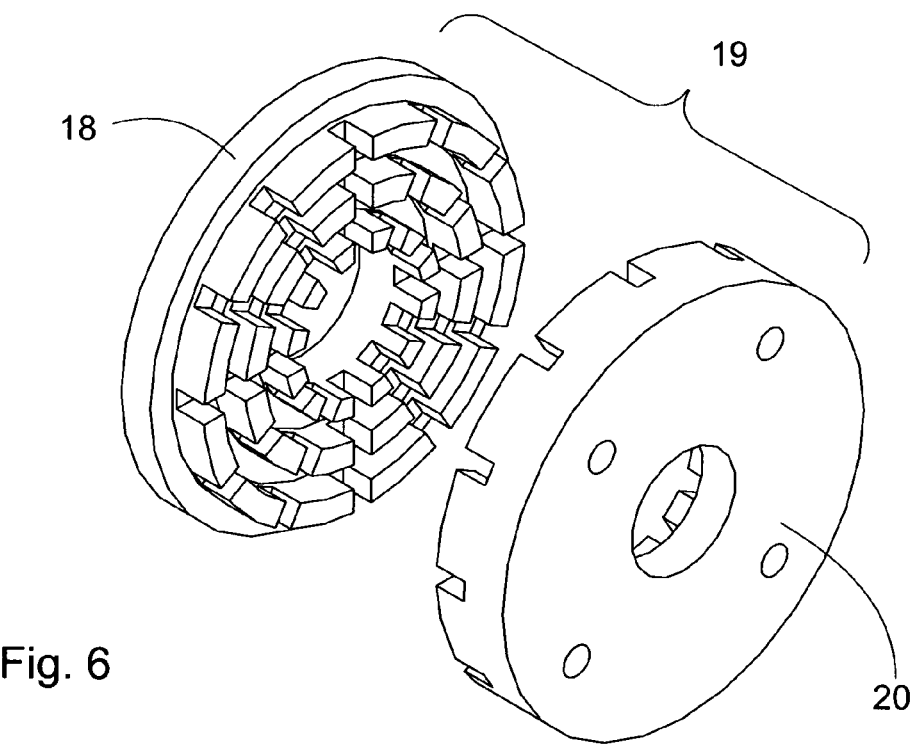
FIG. 6 is an isometric exploded back view of the first mechanical shear stage, according to the present invention.

FIGS. 5 and 6 are isometric front and back views of the first mechanical shear stage 19, according to the present invention.

By means of these two figures it is possible to see how the first stator 18 and the first rotor 20 are placed with the first rotor annular rings 20b going into the first stator annular channels 18c.

The similar configuration is applied for the second rotor 24 and second stator 26 (both not shown in this figure).

FIG. 7 is a schematic side view of the first stator 18, according to the present invention.

This figure shows that the first stator base 18a has a diameter larger than the largest of the first stator annular rings 18b. This is done to accommodate the largest first rotor annular ring 20b.

FIG. 8 is a schematic front view of the first stator 18, according to the present invention.

The first stator 18 includes several first stator annular rings 18b separated by the several first stator annular channels 18c. The first stator annular rings 18b and the first stator annular channels 18c are intersected by several first stator flow channels 18d that have a generally perpendicular direction with respect to the first stator annular rings 18b and the first stator annular channels 18c, however, the present invention is not limited to straight or purely radial flow channels.

The first stator 18 may contain several first stator fastening screw holes 18f used to mount the first stator 18 to the casing 56 (not shown in this figure).

FIG. 9 is a schematic front view of the first rotor 20, according to the present invention.

The first rotor 20 includes several first rotor annular rings 20b separated by the several first rotor annular channels 20c. The first rotor annular rings 20b and the first rotor annular channels 20c are intersected by several first rotor flow channels 20d that have a generally perpendicular direction with respect to the first rotor annular rings 20b and the first rotor annular channels 20c.

The first rotor 20 may contain several first rotor fastening screw holes 20f used to mount the first rotor 20 to the rotor disk 30 (not shown in this figure).

FIG. 10 is a schematic side view of the first rotor 20, according to the present invention.

The first stator base 18a has substantially the same diameter as the largest of the first rotor annular rings 20b. This is done to accommodate the largest of the first stator annular ring 18b.

Figure 11:
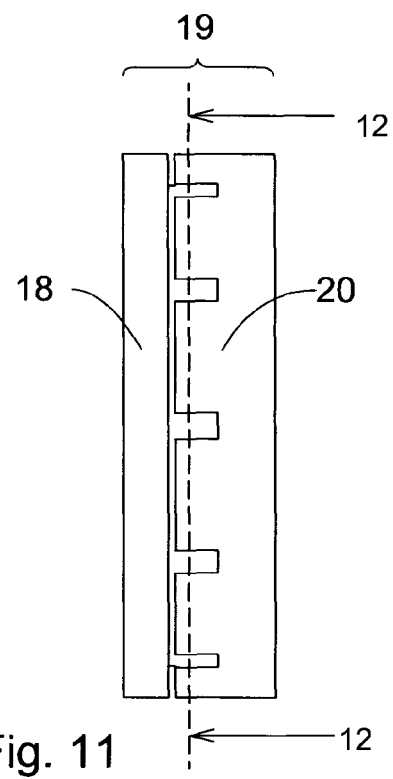
FIG. 11 is a schematic side view of the first mechanical shear stage, according to the present invention, upon which the section plane 12-12 is marked.

FIG. 11 is a schematic side view of the first mechanical shear stage 19, according to the present invention, upon which the section plane 12-12 is marked.

This figure shows the relative positioning of the first stator 18 and first rotor 20 which together comprise the first mechanical shear stage 19.

Figure 12:
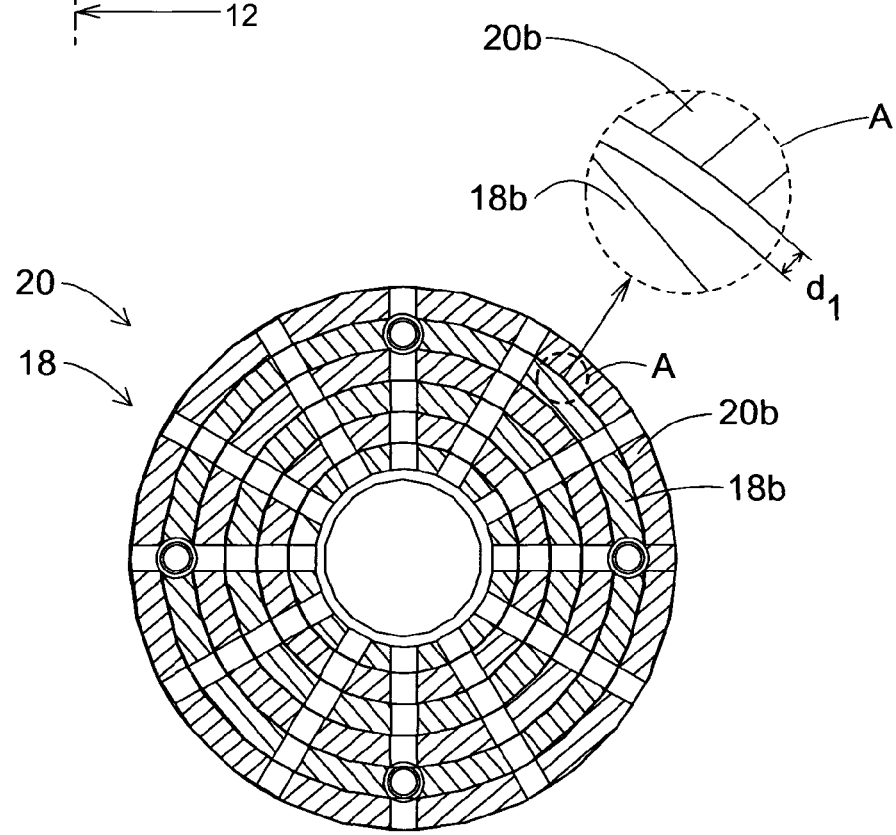
FIG. 12 is a cross sectional view 12-12 through the first mechanical shear stage of FIG. 11, according to the present invention. The illustration marks detail A in a circle, which is magnified in the circle on the top-right side of the illustration.

FIG. 12 is a cross sectional view 12-12 through the first mechanical shear stage 19 of FIG. 11, according to the present invention.

The illustration marks detail A in a circle, which is magnified in the circle on the top-right side of the illustration. Detail A shows the d1 dimension which is the radial distance between the first stator annular rings 18b and the first rotor annular ring 20b.

A typical value of d1 is in the magnitude of one tenth of a millimeter.

Figure 13:
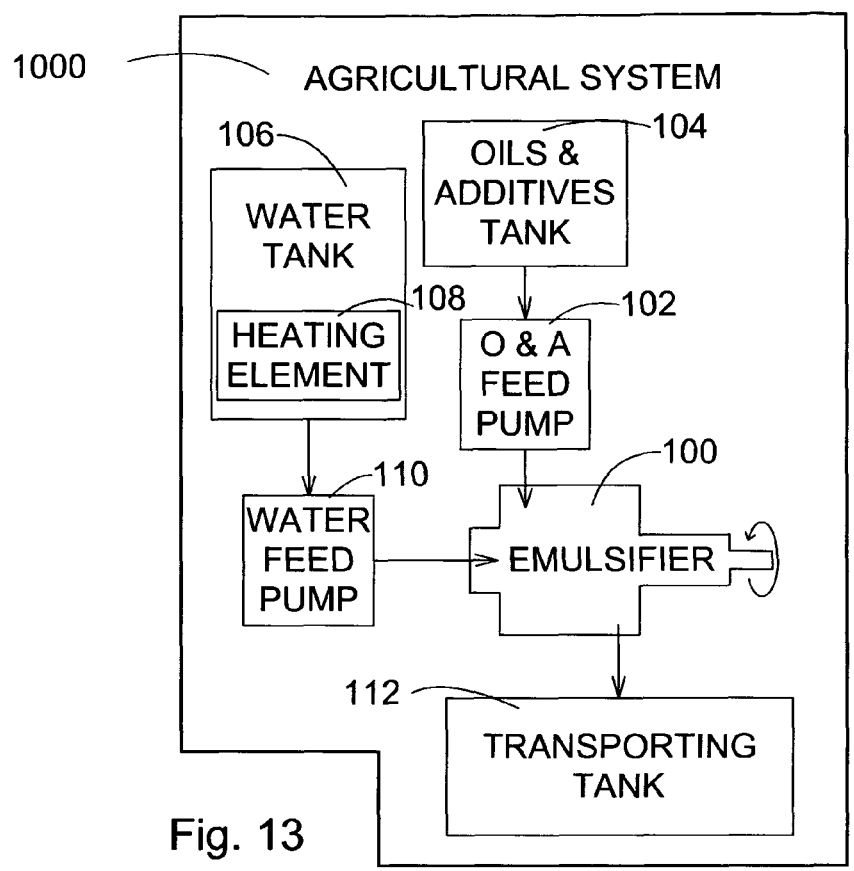
FIG. 13 is a schematic block diagram of a first exemplary embodiment of an agricultural system for manufacturing of emulsions into a transportation tank, according to the present invention.

FIG. 13 is a schematic block diagram of a first exemplary embodiment of an agricultural system 1000 for manufacturing emulsions in a transporting tank 112, according to the present invention.

In this system, water is heated in the water tank 106 by a heating element 108. Hot water is needed in order to heat the oils and additives and ease the shearing of the oils and additives drops in the emulsifier 100.

The heated water is injected into the emulsifier 100 through a water feed pump 110. The water pressure needed for normal operation is between 1 and 10 atmospheres.

Oils and additives are kept in the oils and additives tank 104 and are injected into the emulsifier 100 using the oils and additives feed tank 102. The pressure needed for normal operation is between 2 and 20 atmospheres.

The emulsifier 100 mixes and shears the water and oils and additives to make the emulsion and deposits it into the transporting tank 112.

Figure 14:
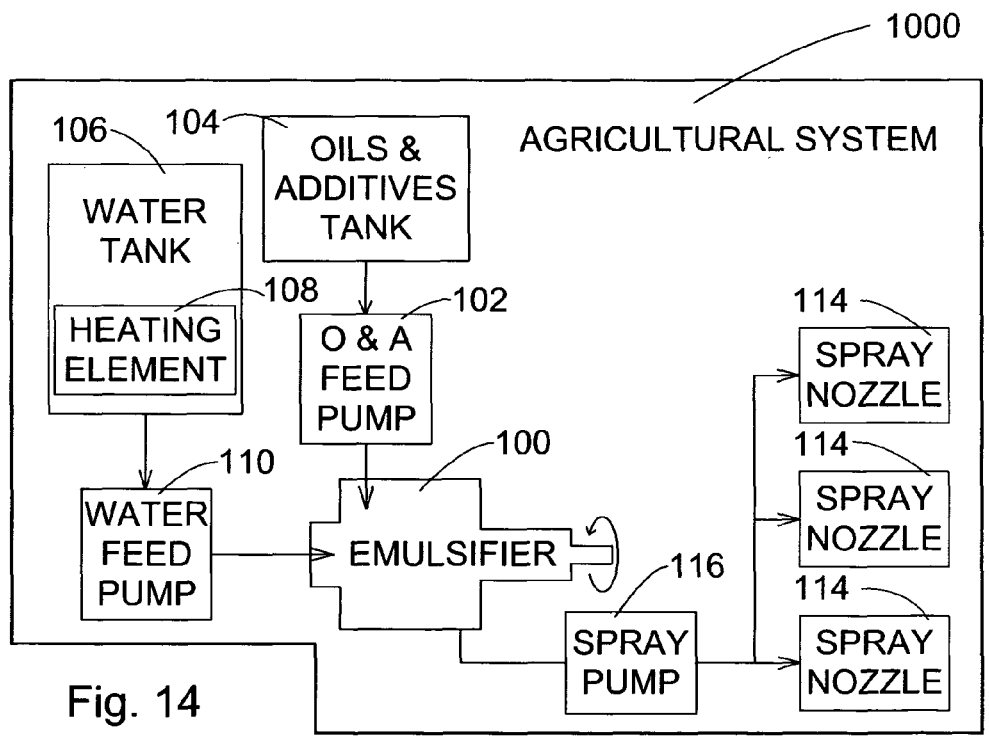
FIG. 14 is a schematic block diagram of a second exemplary embodiment of an agricultural system for in-line manufacturing of emulsions for immediate delivery through spray nozzles, according to the present invention.

FIG. 14 is a schematic block diagram of a second exemplary embodiment of an agricultural system 1000 for in-line manufacturing of emulsions for immediate delivery through spray nozzles 114, according to the present invention. In this system, water is heated in the water tank 106 by a heating element 108. Hot water is needed in order to heat the oils and additives and ease the shearing of the oils and additives drops in the emulsifier 100.

The heated water is injected into the emulsifier 100 through a water feed pump 110. The water pressure needed for normal operation is between 1 and 10 atmospheres.

Oils and additives are kept in the oils and additives tank 104 and are injected into the emulsifier 100 using the oils and additives feed tank 102. The pressure needed for normal operation is between 2 and 20 atmospheres. The emulsifier 100 mixes and shears the water and oils and additives to make the emulsion and deposits it into the spray pump 116 that injects the emulsion through the spray nozzles 114 onto the foliage.

Figure 15:
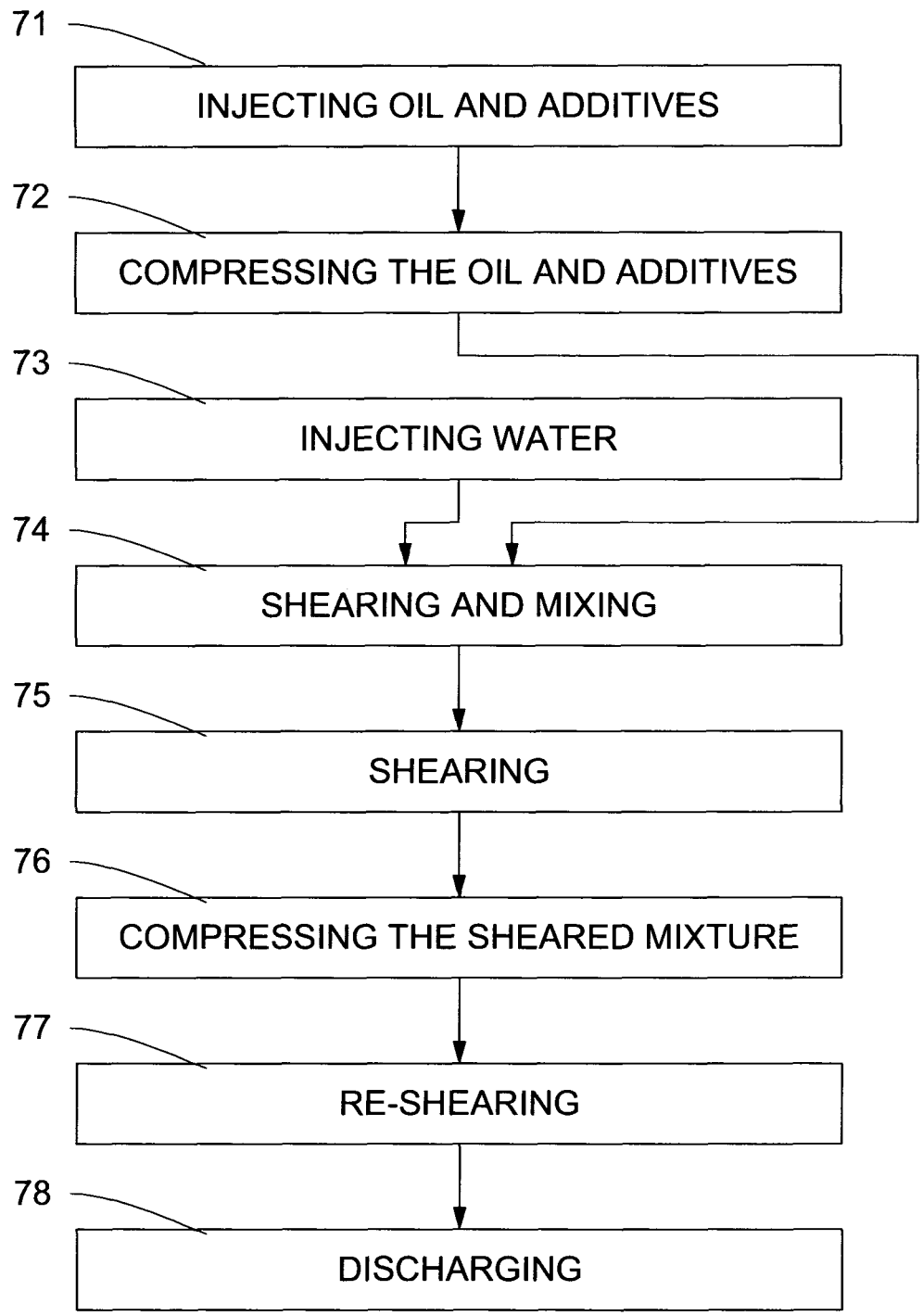
FIG. 15 is a flow chart that schematically illustrates a production process of emulsions in accordance with an embodiment of the present invention.

FIG. 15 is a flow chart that schematically illustrates a production process of emulsions in accordance with an embodiment of the present invention.

The beginning of the emulsions production process is injecting the oils and additives into the oil intake 12 (stage 71) and compressing them into the porous filter 14 (stage 72). At the same time, the system injects the heated water into the water intake 10 (stage 73). Next, the water shears the oils and additives into drops as they exit the porous filter 14 are mixed in the narrow channel 16 (stage 74). The mixture is compressed into the first mechanical shear stage 19 where the rotational movement of the first rotor 20 within the first stator 18 causes the mixture to be sheared into droplets (stage 75) and is forced outwards by the centrifugal force in a relatively short time and is then compressed into the intermediate channel 22 (stage 76). From there, the mixture is compressed into the second mechanical shear stage 25 in an opposite direction to the centrifugal force. Compressing the mixture opposing the centrifugal force takes a relatively long time, causing the mixture to spend more time within the second mechanical shear stage 25 causing it to shear more times and eventually create droplets which are very consistent in size (stage 77). The final emulsion product is discharged through the discharge channel 27 and emulsion discharge pipe 28 outside of the emulsifier 100 (stage 78).

The emulsifier's 100 elements are not shown in this figure but are all shown in other figures.

The emulsions manufactured by the present invention can be used as agricultural pesticides and insecticides to be sprayed onto foliage. However the emulsions manufactured by the present invention are not limited only to agricultural use.

The oils and additives are based primarily on botanical sources however can include other sources, such as fish oil, and the final product is an emulsion for use including at least one oil, additives and water, wherein the oil is in droplets phase, having a volume medium diameter, wherein the volume medium diameter is at least one micron and at most fifteen microns.

The botanical oil may be edible botanical oil which may be one of the oils in the following list:

Peanut oil, cottonseed oil, neem oil, soybean oil, canola (rapeseed) oil, sunflower oil, olive oil, sesame oil, corn oil, linseed oil, palm kernel oil, rice bran oil, grape seed oil, tea tree oil, pumpkin seed oil, argan oil, limeseed oil, nut oils, eucalyptus oil, citronella oil, and citrus oil.

The percentage of the oil is typically less than ten percent of the final emulsion and the percentage the additive is typically less than six-tenths percent of the final emulsion weight; however these values are not in any way limiting the present invention.

Figure 16:
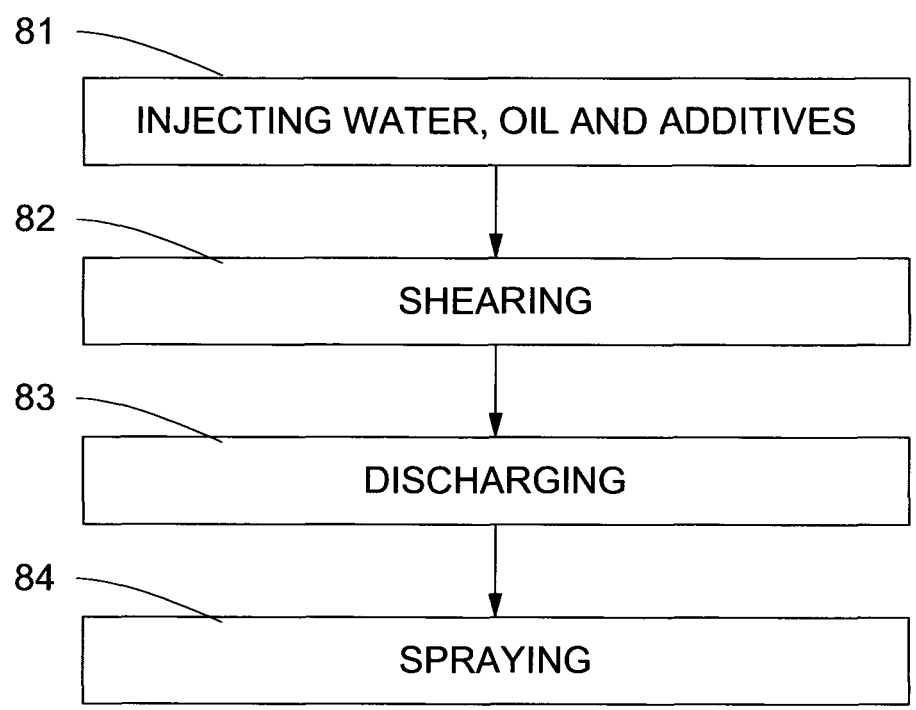
FIG. 16 is a flow chart that schematically illustrates a method for preparation of emulsions for agricultural use, and spraying the emulsions, in accordance with an embodiment of the present invention.

FIG. 16 is a flow chart that schematically illustrates a method for preparation of emulsions for agricultural use, and spraying the emulsions, in accordance with an embodiment of the present invention.

The method includes the main stages of injecting water, oil and additive into an emulsifier, (stage 81), shearing the oil into oil emulsion droplets, (stage 82), discharging final emulsion product outside of the emulsifier, wherein the oil is a botanical oil, wherein the oil emulsion droplets have a volume medium diameter, and wherein the volume medium diameter is at least one micron and at most fifteen microns, (stage 83) and spraying said emulsions on vegetation (stage 84), wherein the emulsions contains at most two-tenths percent of acidic material, for the emulsion weight, or is substantially free of acidic materials.

While the invention has been described with respect to a limited number of embodiments, it will be appreciated that many variations, modifications and other applications of the invention may be made.

What is claimed is:

1. An agricultural system comprising:
   (a) an emulsifier, wherein said emulsifier includes:
      (i) a casing, having water intake, oil intake and discharge channel, wherein said casing includes:
         a main body;
         a front cover, attached to said main body; and
         a back cover attached to said main body;
      (ii) a pivot axis for transferring rotational motion to at least one rotational element of said emulsifier, mounted at least partially inside said emulsifier;
      (iii) a porous filter mounted inside said emulsifier so that when oil is injected and forced to flow through said oil intake, said oil is flowing through said filter into a tight fit space between said pivot axis and said porous filter;
      (iv) a first mechanical shear stage mounted inside said emulsifier, wherein said first mechanical shear stage includes:
         a first stator having at least two first stator annular rings said at least two first stator annular rings interlace with at least one first stator annular channel, and wherein said first stator has at least one first stator flow channel, crossing said at least two first stator annular rings; and
         a first rotor having at least two first rotor annular rings wherein said at least two first rotor annular rings interlace with at least one first rotor annular channel, and wherein said first rotor has at least one first rotor flow channel, crossing said at least two first rotor annular rings;
      (v) a second mechanical shear stage mounted inside said emulsifier, wherein said second mechanical shear stage includes:
         a second stator having at least two second stator annular rings said at least two second stator annular rings interlace with at least one second stator annular channel, and wherein said second stator has at least one second stator flow channel, crossing said at least two second stator annular rings; and
         a second rotor having at least two second rotor annular rings wherein said at least two second rotor annular rings interlace at least one second rotor annular channel, and wherein said second rotor has at least one second rotor flow channel, crossing said at least two second rotor annular rings, wherein said second mechanical shear stage is arranged so that a second rotor annular ring can rotate inside a second rotor annular channel; and
      (vi) a rotor disk attached to said pivot axis, wherein said first rotor is attached to said rotor disk and wherein said second rotor is attached to said rotor disk, wherein said emulsifier has an intermediate channel between said casing and said first mechanical shear stage, said rotor disk, and said second mechanical shear stage,
   wherein said pivot axis, said main body, said first mechanical shear stage, said rotor disk and said second mechanical shear stage define a flow path that enable fluids to flow from said tight fit space to said discharge channel through said first mechanical shear stage outwards along said at least one first stator flow channel, through said intermediate channel, and through said second mechanical shear stage, inwards along said at least one second stator flow channel.

2. The agricultural system of claim 1 wherein there is a gap between each neighbors of said at least two first stator annular rings and said at least two first rotor annular rings, wherein said gap is at most one tenth of a millimeter.

3. The agricultural system of claim 2 further comprising:
   (b) an oils and additives tank;
   (c) an oils and additives feed pump, wherein said oils and additives tank is operatively connected to said oils and additives feed pump and wherein said oils and additives feed pump is operatively connected to said emulsifier;
   (d) a water tank;
   (e) a water feed pump, wherein said water tank is operatively connected to said water feed pump and wherein said water feed pump is operatively connected to said emulsifier; and (f) a spray pump, wherein said emulsifier is operatively connected to said spray pump; and
(g) at least one spray nozzle, wherein said spray pump is operatively connected to said at least one spray nozzle.

4. The agricultural system of claim 2 further comprising:
(b) an oils and additives tank;
(c) an oils and additives feed pump, wherein said oils and additives tank is operatively connected to said oils and additives feed pump and wherein said oils and additives feed pump is operatively connected to said emulsifier;
(d) a water tank;
(e) a water feed pump, wherein said water tank is operatively connected to said water feed pump and wherein said water feed pump is operatively connected to said emulsifier; and
(f) a transporting tank, wherein said emulsifier is operatively connected to said transporting tank.

5. The agricultural system of claim 2 further comprising:
(b) an oils and additives tank;
(c) an oils and additives feed pump to inject oils and additives into said emulsifier, wherein said oils and additives tank is operatively connected to said oils and additives feed pump and wherein said oils and additives feed pump is operatively connected to said emulsifier;
(d) a water tank; and
(e) a water feed pump to inject water into said emulsifier, wherein said water tank is operatively connected to said water feed pump and wherein said water feed pump is operatively connected to said emulsifier.

6. The agricultural system of claim 5 wherein in operation, the sum of hydraulic pressure produced by said oils and additives feed pump, the hydraulic pressure produced by said water feed pump, and hydraulic pressure produced by centrifugal force produced by said first rotor is larger than a the hydraulic pressure produced by the centrifugal force produced by said second rotor.

* * * * *